US012790622B2

(12) United States Patent
Yu et al.

(10) Patent No.: US 12,790,622 B2
(45) Date of Patent: Nov. 10, 2026

(54) **USE OF *GLYCINE SOJA* ZINC FINGER PROTEIN 4 (GsZFP4) OR GENETIC MATERIAL THEREOF**

(71) Applicant: NANJING AGRICULTURAL UNIVERSITY, Nanjing (CN)

(72) Inventors: Deyue Yu, Nanjing (CN); Hao Cheng, Nanjing (CN); Yixiang Pu, Nanjing (CN); Hui Wang, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 92 days.

(21) Appl. No.: 18/867,179

(22) PCT Filed: Jul. 30, 2024

(86) PCT No.: PCT/CN2024/108483
§ 371 (c)(1),
(2) Date: Nov. 19, 2024

(87) PCT Pub. No.: WO2025/213631
PCT Pub. Date: Oct. 16, 2025

(65) Prior Publication Data

US 2026/0078399 A1 Mar. 19, 2026

(30) Foreign Application Priority Data

Apr. 7, 2024 (CN) ......................... 202410405467.8

(51) Int. Cl.
*C12N 15/82* (2006.01)
*C07K 14/415* (2006.01)

(52) U.S. Cl.
CPC ........ *C12N 15/8283* (2013.01); *C07K 14/415* (2013.01); *C12N 15/8205* (2013.01)

(58) Field of Classification Search
None
See application file for complete search history.

(56) References Cited

PUBLICATIONS

Wenxian Wu et al., C3HC4-Type RING Finger Protein NbZFP1 Is Involved in Growth and Fruit Development in Nicotiana benthamiana, PLOS One (2014) vol. 9, Issue 6, pp. 1-9 (Year: 2014).*

* cited by examiner

*Primary Examiner* — Weihua Fan
*Assistant Examiner* — Yanxin Shen
(74) *Attorney, Agent, or Firm* — Tutunjian & Bitetto, P.C.

(57) ABSTRACT

Use of a *Glycine soja* zinc finger protein 4 (GsZFP4) or a genetic material thereof are provided. A gene GsZFP4 encoding the GsZFP4 has the nucleotide sequence of SEQ ID NO: 1. A constructed plant overexpression vector pBA002-GsZFP4 is transformed into soybean. After 21 d of treatment with an SMV strain SC7, it is found that disease symptoms in the soybean overexpressing GsZFP4 are significantly alleviated and the SMV content is significantly reduced, demonstrating resistance to the SMV. In summary, the GsZFP4 may positively regulate soybean resistance to the SMV.

6 Claims, 3 Drawing Sheets

Specification includes a Sequence Listing.

USE OF *GLYCINE SOJA* ZINC FINGER PROTEIN 4 (GsZFP4) OR GENETIC MATERIAL THEREOF

CROSS REFERENCE TO RELATED APPLICATION

The present application is a national stage application of the PCT application No. PCT/CN2024/108483 filed on Jul. 30, 2024, which claims priority to the Chinese Patent Application No. CN202410405467.8, filed with the China National Intellectual Property Administration (CNIPA) on Apr. 7, 2024, and entitled "USE OF GENE GsZFP4 ENCODING *GLYCINE SOJA* ZINC FINGER PROTEIN TRANSCRIPTION FACTOR", both of which are incorporated herein by reference in its entirety.

REFERENCE TO SEQUENCE LISTING

A computer readable XML file entitled "GWPCTP-20240806280_seqlist", which was created on Sep. 21, 2024, with a file size of about 17,341 bytes, contains the sequence listing for this application, has been filed with this application, and is hereby incorporated by reference in its entirety.

TECHNICAL FIELD

The present disclosure belongs to the technical field of genetic engineering and relates to use of a *Glycine soja* zinc finger protein 4 (GsZFP4) or a genetic material thereof.

BACKGROUND

During the growth, soybean plants are susceptible to a variety of diseases and environmental stresses. Among the diseases, soybean mosaic virus (SMV)-induced disease can cause serious damage to soybean yield and quality. The yield loss caused by SMV to soybean is generally about 10%, but in severe years, it can reach 35% to 50%, or even lead to total crop failure (Li et al., 2013). Since SMV is widely distributed, causes serious damage, and is difficult to control with chemical agents, breeding and planting disease-resistant varieties is the most economical and effective method to control the SMV-associated diseases.

Wild soybean (*Glycine soja* Sieb. et Zucc.) is a wild relative of cultivated soybean (*Glycine max* (L.) Merr.). China is the origin center of soybean and has rich *Glycine soja* resources. Today, there are more than 6,000 *Glycine soja* resources preserved in China, accounting for not less than 90% of the total amount globally (Ma et al., 2009). Molecular marker analysis has showed that the genetic diversity of *Glycine soja* is higher than that of cultivated soybeans. Comparison of the genetic diversity of *Glycine soja* and local soybean varieties has found that only 51% of the alleles in *Glycine soja* are retained in the local soybean varieties (Wen et al., 2009). Therefore, discovering novel SMV resistance genes from *Glycine soja* resources plays a key role in reducing SMV damage and improving the effectiveness of SMV resistance breeding.

SUMMARY

An objective of the present disclosure is to provide use of a gene GsZFP4 encoding a *Glycine soja* zinc finger protein transcription factor in genetic engineering of disease resistance, where the gene is rapidly upregulated in leaves after SMV induction. In addition, subcellular localization analysis has revealed that GsZFP4 is a nuclear localization protein. The gene GsZFP4 can be introduced into soybean as a target gene to positively regulate soybean resistance to the SMV.

The objective of the present disclosure is achieved by the following technical solutions:

The gene GsZFP4 encoding a *Glycine soja* zinc finger protein transcription factor has the nucleotide NO: sequence of SEQ ID 1, specifically 5'-ATGTCCTCCGAAGACAT-
CACTCTCGTACCCGACCAGAGGATCGAGAACGG-
TCTCAAT TCCCCTCTCGTCTTCCAAGACGACCCT
CTCCGCTTCAATTGCCCCACCCCGCACCAGC GTCG
GGTCGGGGACCCGCCTCCGAAGACCCGCGAACTT
GGCGCCTTCATCGACGAC AACAAGATGTTCATC GA
CCGCGACCGCTTCTTCGCCGCCGCCCAGAACCCC-
GAATTC CGCCGCTACGCCGACTGCTCCGCCCGC CG
CGACCCGCCCCACGCCCGCAATTGGAGC GCCACA-
GACGATGACGAAGAGTCTGACGACGACGACGAA-
GATGACGACGACGATGA AGCGGATGACACCGAAG
TAGGAGGACTCGTTGGTGATGGAACCAAAAGCG
AACTTAACAACAACAACAACGGTGGCGCTAATTT
ACCTGCTGTTGCAAACGGGAAAGCCCACTCTTAC
GTTTCTGGAAGAGAGCTATTGGTGAAGGATGGT
GGTGATATTGGGCAATTGGTGCATAGCAATGTGA
GTGGTGGTGATGAAGATCATCGGCAAGAGGGGT-
TAGGTAAGTC TCAGAATTCAGTTACCGTTGCTGA
AACTGACTGTGAGGAGTACTATTCGCACTATCTT
CACGGCGGCGAAGGGGCTTCTGGGCAGAAAGT-
GATGGTGGATGATAGTGGTTGTGG GTTTAGTGG-
GAGGAAGGATGCTATGTATTCGAGCGAGTCAGGG-
GAGTCACTCAGGGC AATTCTTTCAGATCCTGTCAC
GGGTGCTCTTATGGATGATGCTATGATATTAC-
CATGTGG ACATTCATTTGGTGGAGGTGGAATAGAG-
CATGCTATTAGAATGAAAGCTTGCTGCACTTGTT
CTCAACCCACAACTGAGGAATCAATATCTCCAA
ACCTATCACTCCGGATTGCTG TGCAGGCATATCG-
TCGTGAAGAGGAGTCACAATTTTACCGGTCACCT-
AAAAGAAGAA GAGAGAGATTTGATCAGGGTGG-
TTTTGGAGATTCAGTTGTTATGGAACCATCAAGGA
GTAGAGGTGTTCAGTTTCCATTTGCTGTGATGG-
ACCGGGTTATCATAAAGGGAAATAA AAGGACAC-
CACAACGCTTTGTTGGGCGCGAAGCTATTGTTA-
CAACGCAATGCCTGAA TGGATGGTATGTGGTGAA-
GACATTGGACAATGCAGAGAGTGTAAAGTTGCAG-
TATCG ATCCCTTGCCAAGGTTATGGATGATCCTT-
CAAAACCTGCAGCCTCCAGCAAGATGCCA CCTA-
ATTGGCTTTAG-3'. The gene GsZFP4 encoding the *Glycine soja* zinc finger protein transcription factor encodes a *Glycine soja* zinc finger protein 4 (GsZFP4) having the amino acid sequence of SEQ ID NO: 2, specifically

MSSEDITLVPDQRIENGLNSPLVFQDDPLRFNCPTPHQRRVGDPPPKTR

ELGAFIDDNKMFIDRDRFFAAAQNPEFRRYADCSARRDPPHARNWSATD

DDEESDDDDEDDDDDEADDTEVGGLVGDGTKSELNNNNNGGANLPAVAN

GKAHSYVSGRELLVKDGGDIGQLVHSNVSGGDEDHRQEGLGKSQNSVTV

AETDCEEYYSHYLHGGEGASGQKVMVDDSGCGFSGRKDAMYSSESGESL

RAILSDPVTGALMDDAMILPCGHSFGGGGIEHAIRMKACCTCSQPTTEE

SISPNLSLRIAVQAYRREEESQFYRSPKRRRERFDQGGFGDSVVMEPSR

SRGVQFPFAVMDRVIIKGNKRTPQRFVGREAIVTTQCLNGWYVVKTLDN

AESVKLQYRSLAKVMDDPSKPAASSKMPPNWL*.

The present disclosure further provides a recombinant expression vector, including the gene GsZFP4 encoding the *Glycine soja* zinc finger protein transcription factor.

When the gene GsZFP4 is used to construct a plant expression vector, any enhanced promoter or inducible promoter can be added before a transcription initiation nucleotide of the gene. In order to facilitate identification and screening of a transgenic plant cell or plant, the used plant expression vector can be processed, for example, selectable marker genes (a GUS gene, a luciferase gene and the like) can be added. Given the safety of transgenic plants, it is possible to directly screen transformed plants under adversity without adding any selectable marker gene.

The plant expression vector carrying the gene GsZFP4 in the present disclosure can be transformed into plant cells or tissues by conventional biological methods, such as Ti plasmid, Ri plasmid, plant viral vector, DNA transformation, microinjection, electroporation, and *Agrobacterium*-mediated transformation, and then obtained transformed plant tissues are cultured into plants. The transformed plant host can be a monocotyledonous plant such as sorghum, rice, wheat, and corn, or a dicotyledonous plant such as peanut, soybean, rapeseed, tomato, poplar, turf grass, and alfalfa.

In the present disclosure, after the gene GsZFP4 encoding the *Glycine soja* zinc finger protein transcription factor is transformed into soybean through genetic engineering, it is found that the gene GsZFP4 positively regulates soybean resistance to the SMV.

Beneficial Effects

GsZFP4 in *Glycine soja* is a zinc finger protein (ZFP) transcription factor that positively regulates the resistance of transgenic soybean to SMV strain SC7. The gene is rapidly upregulated in leaves after SMV induction, and subcellular localization analysis has revealed that GsZFP4 is a nuclear localization protein. Functional verification has also revealed that GsZFP4 positively regulates the resistance of transgenic soybean to SMV. Therefore, GsZFP4 can be used as a target for regulating soybean resistance to SMV and for the modification of soybean resistance to SMV.

BRIEF DESCRIPTION OF THE DRAWINGS

To illustrate the embodiments of the present application or the technical solutions in the prior art more clearly, the drawings required in the examples will be briefly introduced below.

DETAILED DESCRIPTION OF THE EMBODIMENTS

The following describes the present disclosure with reference to the accompanying drawings and examples.

Methods used in the following examples are conventional methods unless otherwise specified.

Example 1

Cloning and expression characteristics analysis of GsZFP4 gene in *Glycine soja*

1) Cloning of the Gene GsZFP4 Encoding the *Glycine soja* Zinc Finger Protein Transcription Factor According to the gene ID Glysoja.04G010500 of GsZFP4, the corresponding base sequence of the gene was found in the Soybase database, and specific primers F1: 5'-CTCGTCGTACAATCCATCTC-3' (SEQ ID NO: 3) and F2: 5'-CATTTCCACTCAAACATTTATC-3' (SEQ ID NO: 4) were designed based on the sequence.

A *Glycine soja* material NJAU_W052 was used as a sampling material, its leaves were ground with a mortar and then added to a 1.5 mL EP tube containing lysis solution. After sufficient shaking, the lysed leaves were transferred to a 1.5 mL EP tube to extract the total RNA (Tiangen, Beijing, China). The mass of total RNA was identified by formaldehyde denaturing gel electrophoresis, and the RNA content was determined by a spectrophotometer.

Figure 1:
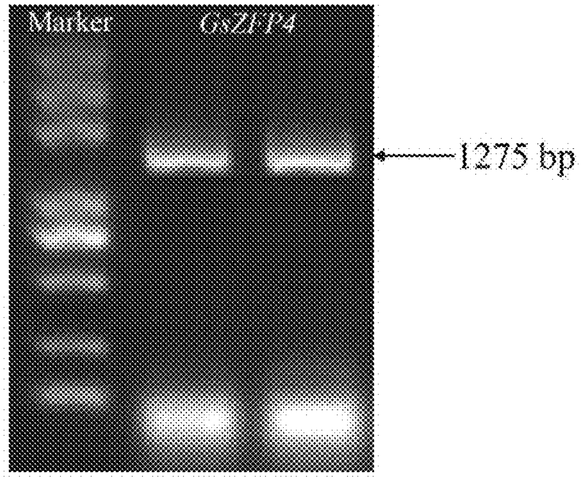
FIG. 1 shows a polymerase chain reaction (PCR) amplification result of the GsZFP4 gene: where the Marker is 5,000 bp, and a target band of the GsZFP4 gene is 1,275 bp.

The total RNA obtained was used as a template, and reverse transcription was conducted according to the instructions of a reverse transcription kit provided by Takara. After the first chain of cDNA was obtained, PCR amplification was conducted with a PCR program as follows: initial denaturation at 95° C. for 3 min: 35 cycles of a process including denaturation at 95° C. for 15 s, annealing at 60° C. for 15 s, and extension at 72° C. for 1 min and 30 s: incubation at 72° C. for 5 min, followed by constant-temperature treatment at 12° C. The PCR products were then purified, ligated, and transformed, and positive single clones were selected for sequencing. After the sequencing, the coding sequence (CDS) of the GsZFP4 gene from *Glycine soja* with a complete coding region of 1,275 bp was obtained (SEQ ID NO: 1), and the PCR amplification results are shown in FIG. 1. The gene sequence was synthesized by Beijing Tsingke Biotech Co., Ltd. to allow subsequent vector construction.

2) Subcellular Localization Analysis of GsZFP4

Primers containing the complete open reading frame (ORF) of the GsZFP4 gene (excluding stop codon), F3: 5'-ACAAATCTATCTCTCTCGAGATGTCCTCCGAAGACATCAC-3' (SEQ ID NO: 5) and F4: 5'-GCTCACCATG- GATCCAAGCCAATTAGGTGGCATCT-3' (SEQ ID NO: 6) were designed. The specific PCR process was the same as in step 1).

Figure 2:
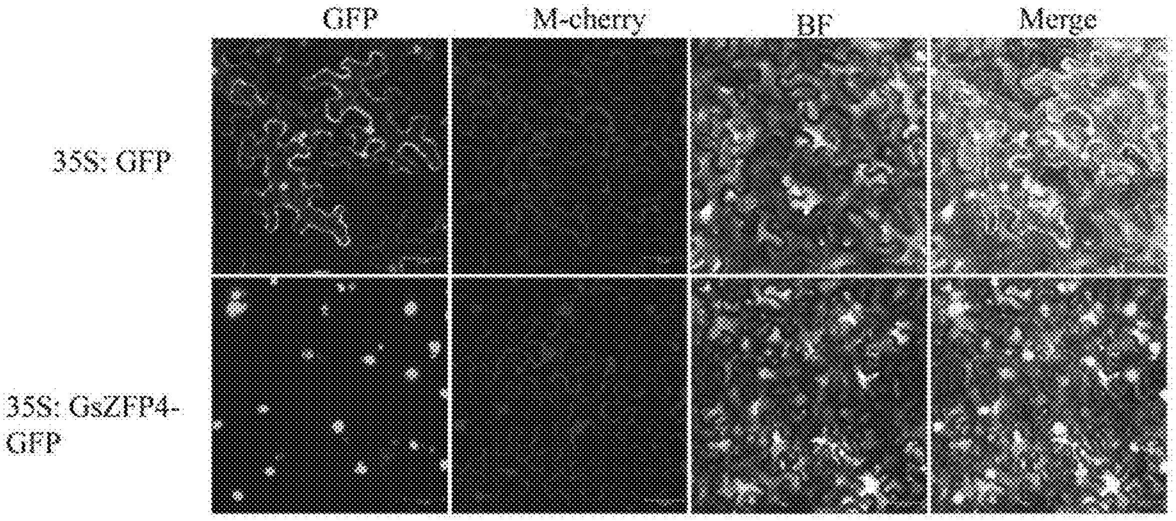
FIG. 2 shows subcellular localization of the GsZFP4 gene: where GFP: green fluorescent protein: M-cherry: red fluorescent protein: BF: bright field: Merge: fusion protein: 35S: GFP: empty control: 35S: GsZFP4-GFP: GsZFP4 protein with a GFP tag: scale bar: 50 μm.

The complete ORF of the GsZFP4 gene without the stop codon was homologously recombined into an expression vector pFGC5941 by double restriction digestion with XhoI and BamHI. In this way, the complete ORF of the GsZFP4 gene was fused with the 3'-end of the reporter gene GFP on the expression vector pFGC5941 to form a chimeric gene of 35S-GsZFP4-GFP, and then a subcellular localization vector pFGC5941-GsZFP4 was constructed. The subcellular localization vector and an empty vector were used to transform the target gene GsZFP4 into tobacco leaf cells using the *Agrobacterium*-mediated transformation. The results showed that the GsZFP4 protein was localized in the cell nucleus (FIG. 2).

3) Expression Analysis of GsZFP4 after SMV Induction

The resistant material NJAU_W052 and the susceptible material HAAS_075 were inoculated with SMV-SC7 to detect the difference in the expression level of GsZFP4 between the resistant and susceptible materials. The treated leaves were collected at 0 h, 2 h, 4 h, 8 h, 12 h, and 48 h after treatment, snap-frozen in liquid nitrogen, and then stored at −80° C. The extraction of total RNA was the same as that in step 1).

The soybean constitutively expressed Tubulin (Accession No. AY907703) was used as an internal reference, and the primers were F5: 5'-GGAGTTCACAGAGGCAGAG-3' (SEQ ID NO: 7) and F6: 5'-CACTTACGCATCACATAGCA-3' (SEQ ID NO: 8). Total RNA from leaves of disease-resistant material NJAU_W052 and susceptible material HAAS_075 from *Glycine soja* under different treatment conditions was used as templates and reverse-transcribed into cDNA to allow qRT-PCR using primers F7: 5'-CTATTCGCACTATCTTCACG-3' (SEQ ID NO: 9) and F8: 5'-ATCCTTCCTCCCACTAAACC-3' (SEQ ID NO: 10), to detect the expression changes of GsZFP4 after SMV induction.

Figure 3:
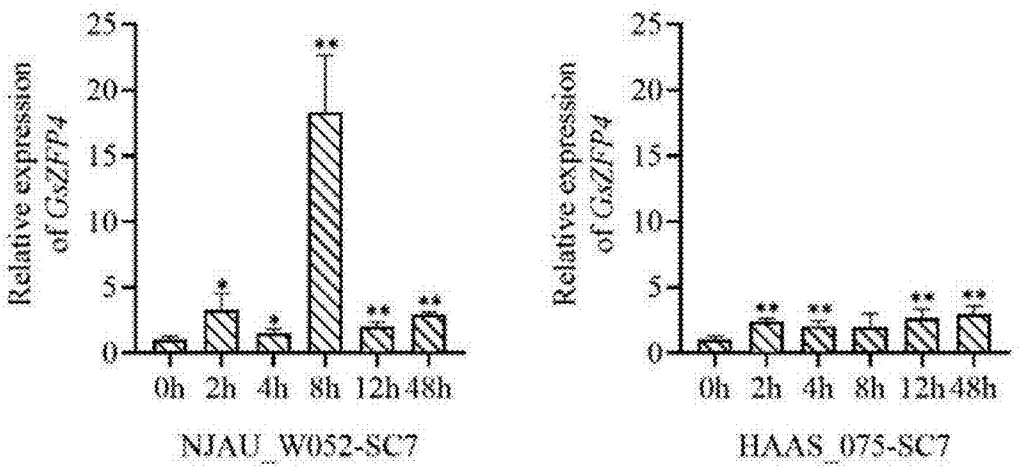
FIG. 3 shows expression levels of GsZFP4 in a disease-resistant material NJAU_W052 and a disease-susceptible material HAAS_075 at 0 h, 2 h, 4 h, 8 h, 12 h, and 48 h after SMV-SC7 induction; where the values are expressed as three biological means±standard error (SE), and * and ** represent significance at the 0.05 and 0.01 probability levels, respectively.

It was found that the expression of GsZFP4 in the disease-resistant material was strongly induced by SMV, reaching a peak at 8 h after virus infection, which was about 18 times that at 0 h (FIG. 3). This indicated that GsZFP4 could actively respond to SMV induction and increase its expression level in disease-resistant materials.

Example 2

Use of Gene GsZFP4 in Genetic Engineering

1) Construction of a Plant Overexpression Vector

Using F9: 5'-CGCGCCGGGCCCAGGCCTACGCGTATGTCCTCCGAAGACATCACTCT-3' (SEQ ID NO: 11) and F10: 5'-ATCGGGGAAATTCGAGCTCCTAAAGCCAATTAGGTGGCATCT-3' (SEQ ID NO: 12) as primers, the CDS of the GsZFP4 gene was obtained by PCR amplification from a PUC19-T Vector containing the CDS of the GsZFP4 gene of SEQ ID NO: 1 from *Glycine soja*, which was synthesized by a biological company. The GsZFP4 was ligated to a pBA002 vector by recombination to obtain a pBA002-GsZFP4 plant overexpression vector. The plant transformation vector pBA002 contained a strong 35S promoter, which could strongly induce the expression of the target gene GsZFP4 in a recipient. The pBA002-GsZFP4 plant overexpression vector was transformed into an *Agrobacterium tumefaciens* strain EHA105 by freeze-thaw method, and soybean was transformed by soybean cotyledonary node transformation.

2) Relative Expression of GsZFP4 Gene in Overexpression Material

Figure 4:
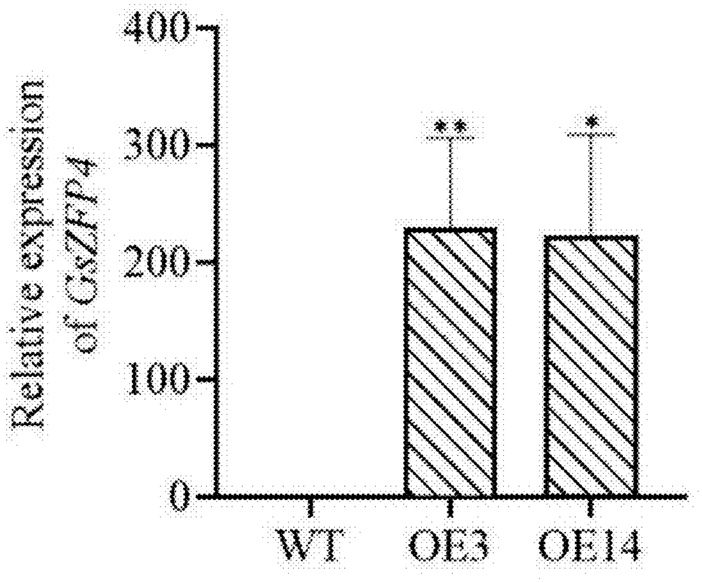
FIG. 4 shows a relative expression level of the GsZFP4 gene in an overexpression material; where OE3 and OE14 represent two GsZFP4-overexpressing lines: the values are expressed as means±standard error (SE) of three biological samples, and * and ** represent significance at the 0.05 and 0.01 probability levels, respectively.

Two stably transformed overexpression positive lines were obtained by tissue culture and named OE3 and OE14. The GsZFP4-overexpressing soybean materials were planted in a constant-temperature basement, and their leaves were taken after 21 d, snap-frozen in liquid nitrogen, and then stored at −80° C. The extraction of total RNA was the same as that in step 1). The soybean constitutively expressed Tubulin was used as an internal reference, and the primer sequences are shown in F5 and F6. The total RNA of GsZFP4-overexpressing soybean material was used as a template, and reverse-transcribed into cDNA to allow qRT-PCR, and the primer sequences are shown in F7 and F8. The changes in the expression level of the GsZFP4 gene in different materials were detected, and FIG. 4 shows that the expression level of the GsZFP4-overexpressing strain was significantly higher than that of the wild type.

3) Phenotype Identification

Figure 5:
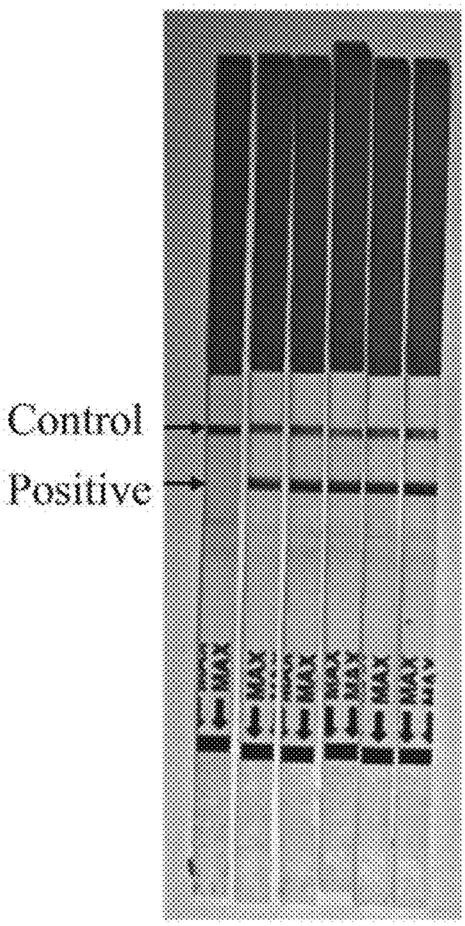
FIG. 5 shows test result of GsZFP4 gene-overexpressing soybean using test strips; where the negative is a control wild type, and the non-transgenic plant has one band.
Figure 6:
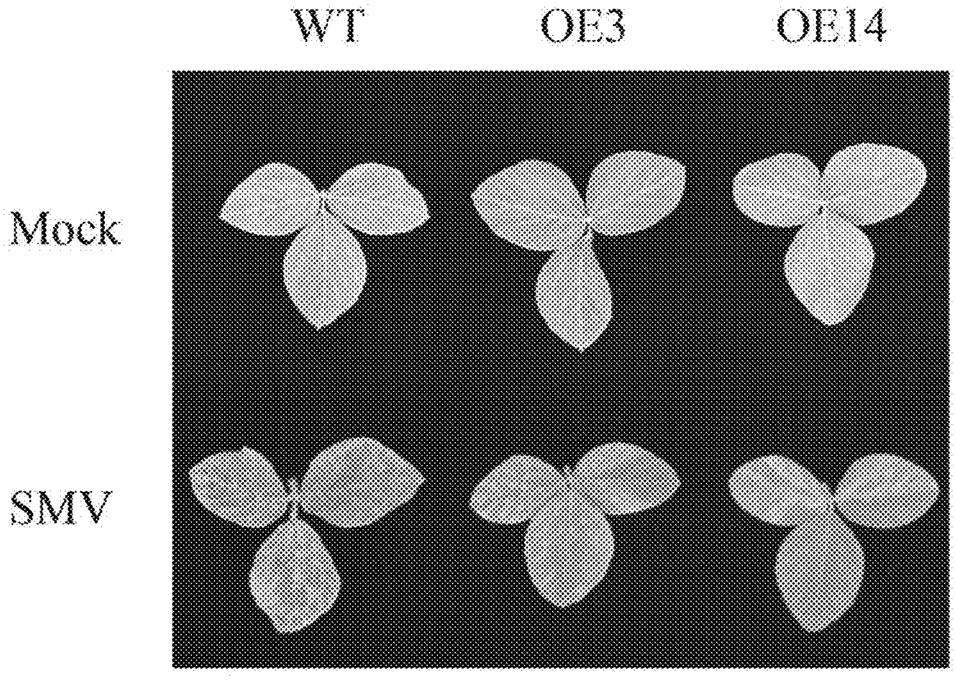
FIG. 6 shows the phenotype of SMV-SC7 resistance of GsZFP4-overexpressing strain 21 d after inoculation.
Figure 7:
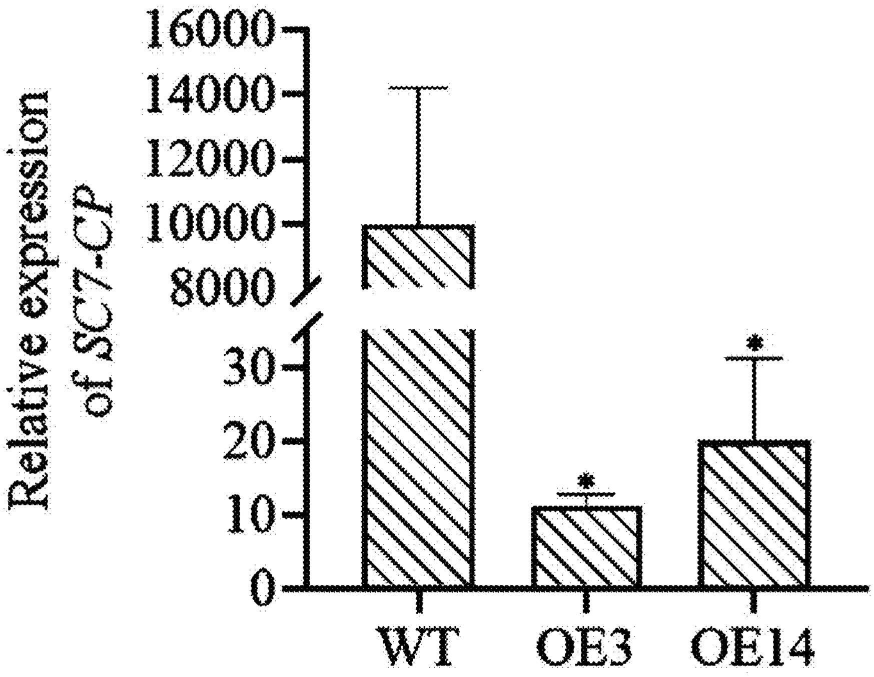
FIG. 7 shows expression of the gene encoding the viral coat protein (CP) in the GsZFP4-overexpressing strain detected by real-time quantitative reverse transcription polymerase chain reaction (qRT-PCR); where the values are expressed as means±standard error (SE) of three biological samples, and * represents significance at the 0.05 probability level.

Through tissue culture, two overexpression lines, OE3 and OE14, were obtained, and overexpression positive seedlings were detected by bar test strips (FIG. 5). After the true leaves were fully expanded, the wild type WT and overexpression strains were inoculated with the SMV-SC7 virus or 0.01 mol/L phosphate-buffered saline (PBS), and the disease development was observed 21 d after inoculation. The leaves of the control plant WT showed obvious wrinkling, while the leaves of the overexpression line did not show obvious mosaic symptoms (FIG. 6). Analysis of the expression levels of the viral CP gene revealed that the expression levels of the SMV-CP gene in the two overexpression lines were significantly lower than that in the wild type (FIG. 7). The primer sequences for detecting the expression level of the SMV-CP gene were shown in F11: 5'-CAGATGGGTGTGGTTATG-3' (SEQ ID NO: 13) and F12: 5'-ACAATGGGTTTCAGCGGATA-3' (SEQ ID NO: 14). The above results indicated that overexpression of the GsZFP4 gene could reduce virus accumulation and improve soybean resistance to SMV-SC7.

Although the present application has been described in detail through the above examples, the examples are merely some rather than all of the embodiments of the present application. All other embodiments obtained by a person based on these examples without creative efforts shall fall within the protection scope of the present application.

REFERENCES

Ma X, Yang G, Yang Z, et al. Application of wild soybean in soybean breeding[J]. Crop Research, 2009, 23(1): 11-13.

Li K, Liu Z, Li H, et al. Resistance to soybean mosaic virus and soybean cyst nematode of soybean cultivars from China national soybean uniform trials[J]. Soybean Science, 2013, 32(5): 670-675.

Wen Z, Ding Y, Zhao T, et al. Genetic diversity and peculiarity of annual wild soybean (*G. soja* Sieb. et Zucc.) from various eco-regions in China[J]. Theoretical and Applied Genetics, 2009, 119:371-381.

What is claimed is:

1. A method for increasing soybean resistance to a soybean mosaic virus (SMV), comprising transforming a soybean plant with *Agrobacterium tumefaciens*, wherein the *Agrobacterium tumefaciens* comprises a plant expression vector comprising a gene of SEQ ID NO: 1 encoding *Glycine soja* zinc finger protein 4 (GsZFP4); and wherein the GsZFP4 has the amino acid sequence of SEQ ID NO: 2.

2. The method according to claim 1, wherein the plant expression vector comprises a vector selected from the group consisting of a pBA002 vector and a PUC19-T vector, and the gene inserted into the vector.

3. The method according to claim 1, wherein the transforming reduces a content of the SMV in the soybean plant.

4. A recombinant bacterium, comprising *Agrobacterium tumefaciens* and the gene or the plant expression vector defined in claim 1 introduced into the *Agrobacterium tumefaciens*.

5. The recombinant bacterium according to claim 4, wherein the *Agrobacterium tumefaciens* is an *Agrobacterium tumefaciens* strain EHA105.

6. The method according to claim 1, wherein the transforming is conducted by soybean cotyledonary node transformation.

* * * * *

SEQUENCE LISTING

```
Sequence total quantity: 14
SEQ ID NO: 1            moltype = DNA  length = 1275
FEATURE                 Location/Qualifiers
source                  1..1275
                        mol_type = other DNA
                        note = Gene GsZFP4
                        organism = synthetic construct
SEQUENCE: 1
atgtcctccg aagacatcac tctcgtaccc gaccagagga tcgagaacgg tctcaattcc  60
cctctcgtct tccaagacga ccctctccgc ttcaattgcc ccaccccgca ccagcgtcgg  120
gtcggggacc cgcctccgaa gacccgcgaa cttggcgcct tcatcgacga caacaagatg  180
ttcatcgacc gcgaccgctt cttcgccgcc gcccagaacc ccgaattccg ccgctacgcc  240
gactgctccg cccgccgcga cccgccccac gcccgcaatt ggagcgccac agacgatgac  300
gaagagtctg acgacgacga cgaagatgac gacgacgatg aagcggatga caccgaagta  360
ggaggactcg ttggtgatgg aaccaaaagc gaacttaaca acaacaacaa cggtggcgct  420
aatttacctg ctgttgcaaa cgggaaagcc cactcttacg tttctggaag agagctattg  480
gtgaaggatg gtggtgatat tgggcaattg gtgcatagca atgtgagtgg tggtgatgaa  540
gatcatcggc aagaggggtt aggtaagtct cagaattcag ttaccgttgc tgaaactgac  600
tgtgaggagt actattcgca ctatcttcac ggcggcgaag gggcttctgg gcagaaagtg  660
atggtggatg atagtggttg tgggtttagt gggaggaagg atgctatgta ttcgagcgag  720
tcaggggagt cactcagggc aattctttca gatcctgtca cgggtgctct tatggatgat  780
gctatgatat taccatgtgg acattcattt ggtggaggtg gaatagagca tgctattaga  840
atgaaagctt gctgcacttg ttctcaaccc acaactgagg aatcaatatc tccaaaccta  900
tcactccgga ttgctgtgca ggcatatcgt cgtgaagagg agtcacaatt ttaccggtca  960
cctaaaagaa gaagagagag atttgatcag ggtggttttg gagattcagt tgttatggaa  1020
ccatcaagga gtagaggtgt tcagtttcca tttgctgtga tggaccgggt tatcataaag  1080
ggaaataaaa ggacaccaca acgctttgtt gggcgcgaag ctattgttac aacgcaatgc  1140
ctgaatggat ggtatgtggt gaagacattg gacaatgcag agagtgtaaa gttgcagtat  1200
cgatcccttg ccaaggttat ggatgatcct tcaaaacctg cagcctccag caagatgcca  1260
cctaattggc tttag                                                   1275

SEQ ID NO: 2            moltype = AA  length = 424
FEATURE                 Location/Qualifiers
source                  1..424
                        mol_type = protein
                        note = GsZFP4
                        organism = synthetic construct
SEQUENCE: 2
MSSEDITLVP DQRIENGLNS PLVFQDDPLR FNCPTPHQRR VGDPPPKTRE LGAFIDDNKM  60
FIDRDRFFAA AQNPEFRRYA DCSARRDPPH ARNWSATDDD EESDDDDEDD DDDEADDTEV  120
GGLVGDGTKS ELNNNNNGGA NLPAVANGKA HSYVSGRELL VKDGGDIGQL VHSNVSGGDE  180
DHRQEGLGKS QNSVTVAETD CEEYYSHYLH GGEGASGQKV MVDDSGCGFS GRKDAMYSSE  240
SGESLRAILS DPVTGALMDD AMILPCGHSF GGGGIEHAIR MKACCTCSQP TTEESISPNL  300
SLRIAVQAYR REEESQFYRS PKRRRERFDQ GGFGDSVVME PSRSRGVQFP FAVMDRVIIK  360
GNKRTPQRFV GREAIVTTQC LNGWYVVKTL DNAESVKLQY RSLAKVMDDP SKPAASSKMP  420
PNWL                                                               424

SEQ ID NO: 3            moltype = DNA  length = 20
FEATURE                 Location/Qualifiers
source                  1..20
                        mol_type = other DNA
                        note = Primer F1
                        organism = synthetic construct
SEQUENCE: 3
ctcgtcgtac aatccatctc                                              20

SEQ ID NO: 4            moltype = DNA  length = 22
FEATURE                 Location/Qualifiers
source                  1..22
                        mol_type = other DNA
                        note = Primer F2
                        organism = synthetic construct
SEQUENCE: 4
catttccact caaacattta tc                                           22

SEQ ID NO: 5            moltype = DNA  length = 40
FEATURE                 Location/Qualifiers
source                  1..40
                        mol_type = other DNA
                        note = Primer F3
                        organism = synthetic construct
SEQUENCE: 5
acaaatctat ctctctcgag atgtcctccg aagacatcac                        40

SEQ ID NO: 6            moltype = DNA  length = 35
FEATURE                 Location/Qualifiers
source                  1..35
                        mol_type = other DNA
```

-continued

```
                       note = Primer F4
                       organism = synthetic construct
SEQUENCE: 6
gctcaccatg gatccaagcc aattaggtgg catct                        35

SEQ ID NO: 7           moltype = DNA  length = 19
FEATURE                Location/Qualifiers
source                 1..19
                       mol_type = other DNA
                       note = Primer F5
                       organism = synthetic construct
SEQUENCE: 7
ggagttcaca gaggcagag                                          19

SEQ ID NO: 8           moltype = DNA  length = 20
FEATURE                Location/Qualifiers
source                 1..20
                       mol_type = other DNA
                       note = Primer F6
                       organism = synthetic construct
SEQUENCE: 8
cacttacgca tcacatagca                                         20

SEQ ID NO: 9           moltype = DNA  length = 20
FEATURE                Location/Qualifiers
source                 1..20
                       mol_type = other DNA
                       note = Primer F7
                       organism = synthetic construct
SEQUENCE: 9
ctattcgcac tatcttcacg                                         20

SEQ ID NO: 10          moltype = DNA  length = 20
FEATURE                Location/Qualifiers
source                 1..20
                       mol_type = other DNA
                       note = Primer F8
                       organism = synthetic construct
SEQUENCE: 10
atccttcctc ccactaaacc                                         20

SEQ ID NO: 11          moltype = DNA  length = 47
FEATURE                Location/Qualifiers
source                 1..47
                       mol_type = other DNA
                       note = Primer F9
                       organism = synthetic construct
SEQUENCE: 11
cgcgccgggc ccaggcctac gcgtatgtcc tccgaagaca tcactct           47

SEQ ID NO: 12          moltype = DNA  length = 42
FEATURE                Location/Qualifiers
source                 1..42
                       mol_type = other DNA
                       note = Primer F10
                       organism = synthetic construct
SEQUENCE: 12
atcggggaaa ttcgagctcc taaagccaat taggtggcat ct                42

SEQ ID NO: 13          moltype = DNA  length = 18
FEATURE                Location/Qualifiers
source                 1..18
                       mol_type = other DNA
                       note = Primer F11
                       organism = synthetic construct
SEQUENCE: 13
cagatgggtg tggttatg                                           18

SEQ ID NO: 14          moltype = DNA  length = 20
FEATURE                Location/Qualifiers
source                 1..20
                       mol_type = other DNA
                       note = Primer F12
                       organism = synthetic construct
SEQUENCE: 14
acaatgggtt tcagcggata                                         20
```